United States Patent [19]

Brendel née Hajnóczki et al.

[11] Patent Number: 4,486,359

[45] Date of Patent: Dec. 4, 1984

[54] PROCESS FOR THE PREPARATION OF N-PHOSPHONOMETHYL-GLYCINE

[75] Inventors: Marta Brendel née Hajnóczki; Imre Gulyás; István Gyökér; Kálmán Zsupán, all of Tiszavasvári; István Csorvássy, Hajdunánás; Zoltán Salamon, Tiszavasvári; Gábor Somogyi, Tiszavasvári; István Szentkirályi, Tiszavasvári; Tibor Timár, Tiszavasvári; Éa Biró née Czapáry, Tiszavasvári; István Fodor, Tiszavasvári; János Répási, Tiszavasvári, all of Hungary

[73] Assignee: Alkaloida Vegyeszeti Gyar, Tiszavasvári, Hungary

[21] Appl. No.: 543,795

[22] Filed: Oct. 20, 1983

Related U.S. Application Data

[63] Continuation of Ser. No. 352,367, Feb. 25, 1982, abandoned, which is a continuation of Ser. No. 166,852, Jul. 8, 1980, abandoned.

[30] Foreign Application Priority Data

Jul. 9, 1979 [HU] Hungary .............................. AA-934

[51] Int. Cl.$^3$ ............................................. C07F 9/38
[52] U.S. Cl. ............................ 260/502.5 F; 562/567; 260/941
[58] Field of Search .................. 260/502.5 F; 562/567

[56] References Cited

U.S. PATENT DOCUMENTS

| | | | |
|---|---|---|---|
| 1,910,331 | 5/1933 | Halbig | 568/851 |
| 2,451,945 | 10/1948 | Hanford | 568/851 |
| 2,796,443 | 6/1957 | Meyer et al. | 568/851 |
| 2,847,442 | 8/1958 | Sallmann | 260/502.5 E |
| 2,877,274 | 3/1959 | Kramis | 568/851 |
| 3,288,846 | 11/1966 | Irani et al. | 260/502.5 F |
| 3,549,728 | 12/1970 | Balde et al. | 260/502.5 E |
| 3,838,124 | 9/1974 | Matzner et al. | 260/502.5 E |
| 4,065,491 | 12/1977 | Pfliegel et al. | 260/502.5 F |
| 4,085,134 | 4/1978 | Redmore et al. | 260/502.5 E |
| 4,237,065 | 12/1980 | Ehrat | 260/502.5 F |

FOREIGN PATENT DOCUMENTS

| | | | |
|---|---|---|---|
| 568570 | 1/1959 | Canada | 562/567 |
| 173170 | 4/1980 | Hungary . | |

OTHER PUBLICATIONS

The Merck Index, 6th ed. (1952), pp. 441, 628, RS 356 M 524.
Essentials of Modern Organic Chemistry, Bonner & Castro Reinhold Publishing, 1967, p. 265.

*Primary Examiner*—J. E. Evans
*Attorney, Agent, or Firm*—Karl F. Ross

[57] ABSTRACT

N-phosphonomethylglycine is prepared from glycine and parsformaldehyde to obtain an intermediate which is reacted with dialkylphosphite to obtain an ester of the desired compound which is then hydrolyzed.

8 Claims, No Drawings

PROCESS FOR THE PREPARATION OF N-PHOSPHONOMETHYL-GLYCINE

This application is a continuation of application Ser. No. 352,367 filed Feb. 25, 1982, now abandoned, which in turn is a continuation of Ser. No. 166,852 filed 07/08/80, now abandoned.

FIELD OF THE INVENTION

The present invention relates to a process for the preparation of N-phosphonomethyl-glycine (glyphosate).

BACKGROUND OF THE INVENTION

N-Phosphonomethyl-glycine, active ingredient of a total herbicide of a wide spectrum may be prepared, for example by the following methods well known in the art:

(a) processes using imino diacetic acid as the starting material (HU-PS No. 165 965, 167 343 and 172 170),
(b) processes employing symmetric N-trisubstituted-triazines (DE-PS No. 2 609 172 and 2 700 017),
(c) Phosphonomethylation of glycine derivatives with chloromethyl-phosphonic acid derivatives (HU-PS No. 174 479).

HU-PS No. 173 170 describes a process in which the product may be obtained by reacting glycine and formaldehyde in an aqueous alkaline medium followed by the reaction of the formed alkali salt of N-hydroxymethyl-glycine with dialkyl phosphite and the hydrolysis of the obtained ester with acid. Though this last process is less complicated then the earlier known processes, when carried out, in large scale it is accompanied by difficulties. As a disadvantage of this last process may be mentioned, that the selectivity of the process is not sufficient and the endproduct is considerably contaminated by glycine, bis-N,N-phosphonomethyl-glycine, etc. and the product must be subjected to further purification in order to get a product of desired purity.

When carrying out the above reaction in large scale the elemental analysis of the product corresponds to the calculated values, but the product contains in fact 26% N,N-bis-phosphonomethyl-glycine and 6% glycine in addition to the desired N-phosphonomethyl-glycine.

The fact that the values correspond to each other can be explained as follows:

Carbon, nitrogen and hydrogen analytical values in the Examples of the mentioned patent specification are substantially the same in the case of this product mixture as in the case of pure N-phosphonomethyl-glycine.

The correct composition of the product mixture has now been determined by liquid chromatography, gas chromatography, and spectroscopy as well as complexometric titrations and analytical methods based upon nitrosation.

In the course of our investigations we observed that dialkyl phosphites rapidly decompose in an aqueous-alkaline medium. Thus, particularly in large scale processes the formation of bis-phosphonomethyl-glycine predominated in aqueous alkaline media.

OBJECT OF THE INVENTION

The object of the invention is to develop the above process further to a large scale technique leading directly to pure products.

DESCRIPTION OF THE DRAWING

The process of the invention for the preparation of N-phosphonomethyl-glycine involves reacting glycine, formaldehyde and dialkyl phosphite and hydrolyzing the obtained N-phosphonomethyl-glycine-ester with an acid. According to the invention the glycine is reacted with formaldehyde in the presence of a $C_{1-4}$ alkanol and the thus obtained N,N-bis-hydroxymethyl-glycine is reacted with dialkyl phosphite in a reaction medium of pH=5–9. The resulting dialkyl-[N-(N-hydroxy-methylene-glycine)-methylene]-phosphite is reacted with a strong mineral acid and the thus formed N-phosphonomethyl-glycine-alkyl ester is hydrolyzed in the presence of a mineral acid and water.

We have now found that glycine and formaldehyde when reacted in an anhydrous medium in the presence of alcohol, form N,N-bis-hydroxy-methyl-glycine, which is a new compound. By employing this new compound in a further reaction which is directed to the preparation of the end-product the possibility of side-reactions may be increasingly eliminated.

We have found further that a dialkyl phosphite may under certain conditions alkylate the possibly present nucleophilic anions, leading thus to side reactions. This possibility should be eliminated.

It could be observed that the above reaction is favorably influenced by the reduction of the ion potential of the cations by further increasing the polarity of the P—O dative bond. It has been further recognized that the reaction is highly dependent on the corresponding pH-value: at a higher pH the possibility of the alkylation side reaction increases, whereas the lower pH-value reduces the selectivity of the phosphonomethylation.

On the basis of the above discoveries we have determined those reaction conditions, under which the reaction takes place as outlined above and the undesired side-reactions are eliminated as effectively as possible.

The solvent's role is very important in the process of the invention. Glycine is reacted with formaldehyde in the presence of $C_{1-4}$ alkanol and at the beginning of the reaction the medium should be anhydrous. As a solvent methanol or ethanol are preferably used. Alkanol may be used in a solvent mixture, for example together with dioxane, tetrahydrofuran, and/or a $C_{1-4}$ ether as well.

The amount of formaldehyde is also of influence. If formaldehyde is employed approximately in equimolar amounts or in a slight excess related to glycine then a part of glycine does not react. In this case glycine may be easily recovered from the reaction mixture by cooling. The reaction mixture is preferably acidified to the isoelectric point of glycine to recover glycine.

It is preferred to use a greater amount of formaldehyde related to the amount of glycine. When using 1.25–5, preferably 1.8–2 mole equivalents of formaldehyde glycine is substantially fully converted to N,N-bis-hydroxy-methyl-glycine. In this case glycine does not have to be recovered from the reaction mixture.

Formaldehyde is preferably prepared from paraformaldehyde in situ.

In the reaction of N,N-bis-hydroxymethyl-glycine and a dialkyl phosphite the base may be selected from various bases, such as alkali hydroxides alkali alcoholates and/or alkali acetates in order to adjust the suitable pH. Sodium hydroxide, sodium alcoholate or more particularly potassium hydroxide, potassium alcoholate, or sodium or potassium acetate buffers may be employed.

The reaction of N,N-bis-hydroxymethyl-glycine and dialkyl phosphite is preferably conducted in the presence of trialkyl amine or any other organic nitrogen-containing base, which is suitable to form a reactive adduct with a dialkyl phosphite, and thus the reaction mixture may be easily processed and a product of good quality may be obtained. The amine base plays a role of a catalyst in the reaction. The tertiary ammonium ion of minimal ion potential promotes the reaction of dialkyl phosphites, as it forms a Lewis acid-base adduct.

Thus the tertiary amine not only ensures the conditions of the optimal pH, but stimulates the reactant itself.

The nitrogen-containing base is generally used in an amount of 0.5–3.0 mole equivalents related to glycine. Cyclic or straight chained tertiary amines, such as diethyl aniline, N-methyl-piperidine, N-methyl-pyrrolidine, triethyl amine, trimethyl amine may preferably be employed.

From a industrial point of view the use of 0.5–1.0 mole equivalent of triethylamine related to glycine is preferred, which is easily available, relatively inexpensive and readily recovered.

As dialkyl phosphite any known substance of this class may be used, dimethyl phosphite or diethyl phosphite are preferred.

In the course of performing the process according to the invention we have observed that the reaction is preferably conducted in a relatively dilute solution. For example a 1.1–1.5 mole methanolic solution related to glycine proved to be suitable.

The preferred amount of glycine and formaldehyde is 1.1–1.9 mole equivalents related to dialkyl phosphite. Dialkyl-[N-(N-hydroxy-methylene-glycine)-methylene]-phosphite obtained in the reaction as an intermediate product has not been disclosed yet. This compound may be reacted with a strong mineral acid whereupon it is rearranged to N-phosphono-methyl-glycine-alkyl ester. The isolation of the intermediate product is not necessary. N-Phosphonomethyl-glycine alkyl ester may be hydrolyzed by methods known per se by heating it in the presence of a mineral acid and water.

The reaction mixture may be processed by methods known per se in organic chemistry. Due to the selectivity of the reaction the reaction mixture may be processed by less complicated methods than in the case of the known processes.

The process according to the present invention has the following advantages when compared with the known processes:

The reaction takes place rapidly in a methanolic medium at 25°–60° C., without side reactions, intensive cooling during the reaction of glycine and formaldehyde is not necessary as opposed to the previous processes.

The product is extremely pure (97–99%).

The reaction may be performed in one apparatus and in a homogeneous layer.

Very simple operations, very short reaction time.

The process may be carried out in a continuous reaction system.

The employed tertiary amine catalyst may be well recovered.

The process is the most advantageous from environmental point of view.

The processing of the reaction mixture is simple.

Yield is high.

SPECIFIC EXAMPLES

The details of the process according to the invention are further illustrated by the following Examples.

EXAMPLE 1

37.5 g. of glycine are added to a hot solution of 500 ml. anhydrous methanol, 47.0 g. of triethylamine and 30.0 g. of paraformaldehyde. N,N-bis-hydroxymethyl-glycine obtained in the reaction mixture is reacted without isolation with 55.0 g. of diethyl-phosphite and the reaction mixture is boiled under stirring for 1 hour. To the obtained solution containing dialkyl-[N-(N-hydroxy-methylene-glycine)-methylene]-phosphite 210 ml. of conc. hydrochloric acid are added and the formed N-phosphonomethyl-glycine-ethyl ester is heated for 1.5 hours at 115° C. to hydrolyze it to N-phosphonomethyl-glycine. The reaction mixture is processed and thus 66–68 g. of N-phosphonomethyl-glycine are obtained in crystalline form, purity: above 96%.

Analysis: $C_3H_8NO_5P$ (mol weight: 169.074): calculated: C 21.31%, H 4.77%, N 8.28%, P 18.32%: found: C 21.2%, H 4.8%, N 8.1%, P 18.2%.

NMR in $D_2O$: at room temperature: P-$CH_2$ 3.12 d (J-12 $H_z$) $CH_2$ 3.7 s

Content: according to nitrosation method by spectrophotometry and polarography min.: 98.5±0.5%, HPLC: min. 98.2±1.5%.

EXAMPLE 2

By using 500 ml. of anhydrous methanol containing 10% tetrahydrofuran, 47.0 g. of triethylamine, 30.0 g. of paraformaldehyde, 37.5 g. of glycine and 55.0 g. of diethylphosphite one may proceed as disclosed in Example 1. 65–66 g. of N-phosphonomethyl-glycine are isolated in crystalline form, purity, above 95%. The quality of the product is identical with the quality of the product obtained according to Example 1.

EXAMPLE 3

To 500 ml. of anhydrous ethanol, 48.0 g. of triethylamine, 30.6 g. of paraformaldehyde are added. The mixture is stirred at boiling temperature and 37.5 g. of glycine are added. N,N-bis-hydroxymethyl-glycine formed in the reaction mixture is reacted without isolation with 69.0 g. of diethyl phosphite and the reaction mixture is stirred for 20 minutes at 80° C. The reaction mixture is further processed as disclosed in Example 1. 60–62 g. of crystalline N-phosphonomethyl-glycine are obtained. Purity: above 98%.

EXAMPLE 4

35 g. (0.875 mole) of sodium hydroxide are dissolved in 1000 ml. of anhydrous methyl alcohol. As a consequence of the dissolving the temperature of the solution elevated to 35°–40° C. Into this solution 33.0 g. (1.10 mole) of paraformaldehyde are introduced which depolymerizes instantly. 82.5 g. (1.1 mole) of glycine are added to the clear solution which is heated under stirring to 60° C. 110 g. (1.00 mole) of dimethyl phosphite are added dropwise at this temperature and the solution is heated under reflux for 60 minutes. The reaction mixture is subsequently cooled to 5° C. and the crystallized glycine is filtered off. Thus 20 g. (0.267 mole) of glycine are obtained, which may be used again.

The filtrate is acidified with 330 ml. (4 moles) of concentrated hydrochloric acid. The suspension is cooled to 10° C. and the precipitated salt is filtered off at this temperature. After washing with methanol 42 g. of pure sodium chloride are obtained.

The filtrate is subjected to atmospheric distillation until the inner temperature achieves 113° to 115° C. The solution is then boiled at this temperature under reflux for 2 hours. The solution is then concentrated by distillation in vacuo in order to remove residual hydrochloric acid.

To the distillation residue 150 ml. of water are added. The product is crystallized under cooling and stirring. The filtered substance is washed with methanol and dried at 80° C.

97.6 g. of N-phosphonomethyl-glycine are obtained.
Purity: 98.2%.
Yield related to dimethyl phosphite: 56.7%.
Yield related to glycine: 68.1%.
Quality of the product corresponds to the quality of the products obtained in the previous Examples.

EXAMPLE 5

50.4 g. (0.9 mole) of potassium hydroxide are dissolved in 1200 ml. of anhydrous methanol. To the solution of elevated temperature 45 g. (1.5 mole) of paraformaldehyde are added and after depolymerization 112.6 g. (1.5 mole) of glycine are added. The mixture is heated to 60° C., 110 g. (1.0 mole) of dimethyl phosphite are added dropwise and the mixture is heated unter reflux for 90 minutes. The reaction mixture is then cooled to 28°–30° C. and under stirring 10 ml. of glacial acetic acid are added. The precipitated glycine is filtered at 10° C. and after washing with methanol 48 g. (0.64 mole) of glycine are recovered which may be used again. 330 ml. (4 moles) of conc. hydrochloric acid are added to the filtrate and the precipitated salt is filtered cold and washed with methanol. 37 g. of pure potassium chloride are obtained. The reaction mixture is then heated for a couple of hours to complete hydrolysis. After processing the reaction mixture 117.9 g. of N-phosphonomethyl-glycine are isolated in crystalline form. Product is of 97.5% purity.

EXAMPLE 6

35.2 g. (0.9 grammatom) metal potassium are dissolved in 1300 ml. anhydrous methanol. Into the solution of elevated temperature 45 g. (1.5 moles) of paraformaldehyde are introduced and after depolymerization 112.6 g. (1.5 moles) of glycine are added. The mixture is heated to 60° C., and at this temperature 110 g. (1.0 mole) of dimethyl phosphite are added dropwise. The solution is boiled for 60 minutes, cooled to 28° C. and 10 ml. of glacial acetic acid are added dropwise under stirring. The precipitated glycine is filtered at 10° C., and after washing with methanol 43.8 g. (0.58 mole) glycine are recovered which may be employed again.

To the filtrate 420 ml. (5 moles) of conc. hydrochloric acid are added and the precipitated salt is filtered cold and washed with methanol and thus 64.8 g. of potassium chloride are obtained. The mixture containing N-phosphonomethyl-glycinemethyl-ester is heated for 2–3 hours until the hydrolysis is ended. The reaction mixture is then processed. 124.5 g. of N-phosphonomethyl-glycine are obtained in crystalline form. Purity: 97.5%.

EXAMPLE 7

To a hot solution of 500 ml. methanol, 98 g. potassium acetate and 30 g. of formaldehyde 37.5 g. of glycine and 55 g. of dimethyl phosphite are added. The mixture is stirred for one hour at the boiling temperature. The mixture is cooled and under cooling 167 ml. conc. hydrochloric acid are added. The solution is stirred for 15 minutes at 5° C. and the precipitated salt is filtered off. One may further proceed as disclosed in Example 1. 54–55 g. of N-phosphonomethyl glycine are obtained. The quality of the product is as given in Example 1.

EXAMPLE 8

19.5 g. (0.35 kmole) of technical potassium hydroxide are dissolved under stirring in 500 l. of anhydrous methanol. 17.3 kg. (0.58 kmole) of technical paraformaldehyde are added to the methanolic alkaline solution which are dissolved after 1–2 minutes of stirring. 43.3 kg. (0.58 mole) of technical glycine are then dissolved while the inner temperature of the system is elevated to 60° C. To the solution thus obtained 42.3 kg. (0.38 kmole) of dimethyl phosphite are added, whereafter the reaction mixture is boiled for 1 hour. The mixture is then cooled to 28°–30° C., 7 l. of glacial acetic acid are added and after crystallization for 30 minutes the precipitated glycine is centrifuged and the mixture is washed on the centrifuge with 20 liters of anhydrous methyl alcohol. After drying 19 kg. (0.25 kmole) of glycine are obtained which may be employed again.

The cold solution is added to 154 kg. (1.48 kmole) of a conc. aqueous technical hydrochloric acid solution under stirring and cooling. The precipitated potassium chloride is crystallized for 30 minutes at 10° C., centrifuged, and the salt is washed with 20 l. of anhydrous methanol on the centrifuge 25.0 kg. of centrifuge wet potassium chloride are obtained (dry substance content: 94%).

The product is isolated in crystalline form after hydrolysis carried out for 2.5 hours with aqueous hydrochloric acid at 110°–120° C. After drying 43 kg. of N-phosphonomethyl-glycine are obtained, containing 97.5% pure product in crystalline form.

Analysis: according to nitrosation method: 97.8±0.5%. HPLC method: 97.9±1.5%.

We claim:

1. A process for the preparation of N-phosphonomethyl-glycine which comprises:
   (i) reacting glycine with paraformaldehyde in a molar ratio of 1:1.8–2 in a reaction system consisting of a $C_1$–$C_4$ alkanol under anhydrous conditions using around 1.1–1.5 moles of glycine per liter of $C_4$–$C_4$ alkanol and an alkali compound selected from the group consisting of a tertiary amine and an alkali acetate wherein the molar ratio of the tertiary amine to glycine is about 0.94:1 and the molar ratio of the alkali acetate to glycine is 2:1 to obtain N,N-bis-hydroxymethyl-glycine;
   (ii) reacting the thus obtained solution containing N,N-bis-hydroxymethyl-glycine at the pH thereof with a dialkyl phosphite whereby the molar ratio of glycine to dialkyl phosphite is about 1:1;
   (iii) treating the reaction mixture thus obtained with hydrochloric acid under conditions sufficient to form an N-phosphonomethyl-glycine-alkyl ester; and
   (iv) thereafter hydrolyzing the formed N-phosphonomethyl-glycine in the presence of hydrochloric acid and water.

2. The process defined in claim 1, wherein in step (i) the $C_1$–$C_4$ alkanol is methanol.

3. The process defined in claim 1, wherein in step (i) the alkali compound is an alkali acetate.

4. The process defined in claim 1, wherein in step (i) the alkali compound is potassium acetate.

5. The process defined in claim 1, wherein in step (i) the alkali compound is a tertiary amine.

6. The process defined in claim 1 wherein in step (i) the alkali compound is triethyl amine.

7. A process for the preparation of N-phosphonomethyl-glycine which comprises reacting glycine with paraformaldehyde in a molar ratio of 1:1.8–2 in a reaction system consisting of methanol under anhydrous conditions using around 1.1–1.5 moles glycine per liter of methanol and an acetate whereby the molar ratio of said alkali acetate to glycine is 2:1 to obtain N,N-bis-hydroxy-methyl glycine, reacting the thus obtained solution containing N,N-bis-hydroxymethyl-glycine at the pH thereof with a dialkyl phosphite whereby the molar ratio of glycine to dialkyl phosphite is 1:1, treating the reaction mixture thus obtained with hydrochloric acid under conditions sufficient to form an N-phosphonomethyl-glycine-alkyl ester, and thereafter hydrolyzing the formed N-phosphonomethyl-glycine-alkyl-ester in the presence of hydrochloric acid and water.

8. The process defined in claim 7 wherein the acetate is potassium acetate.

* * * * *

UNITED STATES PATENT AND TRADEMARK OFFICE
CERTIFICATE OF CORRECTION

PATENT NO. : 4,486,359

DATED : December 4, 1984

INVENTOR(S) : Marta BRENDEL et al

It is certified that error appears in the above-identified patent and that said Letters Patent is hereby corrected as shown below:

On the title page;

In the Abstract, right column, item [57], second line, please correct the spelling of the second word to read:

-- paraformaldehyde --.

Signed and Sealed this

Twenty-third Day of July 1985

[SEAL]

Attest:

DONALD J. QUIGG

Attesting Officer — Acting Commissioner of Patents and Trademarks